United States Patent [19]

Mayer et al.

[11] Patent Number: 5,352,683
[45] Date of Patent: Oct. 4, 1994

[54] METHOD FOR THE TREATMENT OF CHRONIC PAIN

[75] Inventors: David J. Mayer; Donald D. Price; Jianren Mao, all of Richmond, Va.; John W. Lyle, Belmar, N.J.

[73] Assignee: Virginia Commonwealth University Medical College of Virginia, Richmond, Va.

[21] Appl. No.: 27,177

[22] Filed: Mar. 5, 1993

[51] Int. Cl.$^5$ ............................................. A61K 31/485
[52] U.S. Cl. ..................................... 514/289; 514/647
[58] Field of Search ................................. 514/289, 647

[56] References Cited

U.S. PATENT DOCUMENTS

| | | | |
|---|---|---|---|
| 4,316,888 | 2/1982 | Nelson | 424/127 |
| 4,602,909 | 7/1986 | Csillik et al. | |
| 4,769,372 | 9/1988 | Kreek | |
| 4,785,000 | 11/1988 | Kreek | |
| 4,876,276 | 10/1989 | Mechoulam et al. | |
| 4,994,467 | 2/1991 | Zimmerman | 514/284 |
| 5,006,510 | 4/1991 | Ellis | |
| 5,013,540 | 5/1991 | Redburn | 424/10 |
| 5,023,239 | 6/1991 | Ogura et al. | |
| 5,055,481 | 10/1991 | Inukai et al. | |
| 5,068,228 | 11/1991 | Köhler | |
| 5,126,330 | 6/1992 | Ogura et al. | |

OTHER PUBLICATIONS

Hayes et al., "Pretreatment with gangiolsides reduces abnormal nociceptive responses associated with a rodent peripheral mononeuropathy", Pain, 48 (1992) 391–396.

Mao et al., "Post-injury treatment with GM1 ganglioside reduces nociceptive behaviors and spinal cord metabolic activity in rats with experimental peripheral mononeuropathy", Brain Research, 584 (1992) 18–27.

Mao et al., "Intrathecal GM1 ganglioside and local nerve anesthesia reduce nociceptive behaviors in rats with experimental peripheral mononeuropathy", Brain Research, 584 (1992) 28–35.

Mao et al. "Pain-related increases in spinal cord membrane-bound protein kinase C following peripheral nerve injury", Brain Research, 588 (1992) 144–149.

Mao et al., Brain Research, 576 (1992) 254–262.

Primary Examiner—Marianne M. Cintins
Assistant Examiner—William R. A. Jarvis
Attorney, Agent, or Firm—Dilworth & Barrese

[57] ABSTRACT

Chronic pain is alleviated in a mammal suffering therefrom by administering to the mammal a chronic pain alleviating amount of a nontoxic N-methyl-D-aspartate receptor antagonist such as dextromethorphan, dextrorphan, ketamine or pharmaceutically acceptable salt thereof, alone or in combination with a local anesthetic and optionally in sustained release dosage form.

9 Claims, 4 Drawing Sheets

METHOD FOR THE TREATMENT OF CHRONIC PAIN

BACKGROUND OF THE INVENTION

This invention relates to methods for the treatment of chronic pain and its varieties, e.g., neuropathic pain.

Chronic pain is persistent pain which has long outlasted the onset of any known or suspected physical cause, usually by a duration greater than 6 months. It can occur after a known injury or disease or it can occur without any known physical cause whatsoever. Moreover, it can be accompanied by known tissue pathology, such as chronic inflammation that occurs in some types of arthritis, or it can occur long after the healing of the injured tissue which is suspected or known to be the cause of the chronic pain. Chronic pain is a very general concept and there are several varieties of chronic pain related to the musculoskeletal system, visceral organs, skin, and nervous system.

Neuropathic pain is a common variety of chronic pain. It can be defined as pain that results from an abnormal functioning of the peripheral and/or central nervous system. A critical component of this abnormal functioning is an exaggerated response of pain-related nerve cells either in the periphery or in the central nervous system. An example is the pain from causalgia wherein even a light touch to the skin is felt as an excruciating burning pain. Neuropathic pain is thought to be a consequence of damage to peripheral nerves or to regions of the central nervous system. However, abnormal functioning of pain-related regions of the nervous system can also occur with chronic inflammatory conditions such as certain types of arthritis and metabolic disorders such as diabetes. Thus, many types of chronic pain that are related to inflammation can be considered to be at least partly neuropathic pains.

The long term administration of narcotic analgesics to patients suffering from various types of chronic pain, e.g., causalgia, hyperesthesia, sympathetic dystrophy, phantom limb syndrome, denervation, etc., is subject to a number of serious drawbacks including the development of opiate tolerance and/or dependence, severe constipation, and so forth.

U.S. Pat. No. 4,769,372 describes a method for treating chronic pain or chronic cough in a patient while preventing or alleviating the development of constipation or other symptoms of intestinal hypomotility wherein an opioid analgesic or antitussive such as morphine, meperidine, oxycodone, hydromorphone, codeine and hydrocodone is administered to the patient together with an opioid antagonist such as naloxone, naloxone glucuronide and nalmefene glucuronide. However successful this therapeutic combination may be in inhibiting the development of constipation or other symptoms of intestinal hypomotility, it does not address the problems of tolerance and/or dependence that are associated with the long term administration of narcotic analgesics.

Other approaches to the treatment of chronic pain/neuropathic pain have included the administration of a pharmaceutically acceptable acid addition salt or a protonated derivative of at least one microtubule inhibitor such as vinblastine, dexacetoxyvinblastine, vincristine, vindesine, leurosine and N-formyl-leurosine as disclosed in U.S. Pat. No. 4,602,909, (3S,4S)-7-hydroxy$\Delta^6$-tetrahydro-cannabinol homologues and derivatives essentially free of the (3R,4R) form as disclosed in Hayes et al., Pain, 48 (1992) 391–396, Mao et al., Brain Res., 584 (1992) 18–27, 584 (1992) 28–35 and 588 (1992) 144–149 and the N-methyl-D-aspartate (NMDA) receptor antagonist, or blocker, MK801 (the compound 5-methyl-10, 11-dihydro-SH-dibenzo [a,d] cyclohepten-5,10-imine) as disclosed in Mao et al., Brain Res., 576 (1992) 254–262. It may be noted that MK 801 is unsuitable for use as a therapeutic due to its pronounced central nervous system neurotoxicity.

Dextrorphan, the main metabolite of the anticonvulsant dextromethorphan, and ketamine are known NMDA receptor antagonists but unlike MK 801, have few, if any, neurotoxic side effects. Heretofore there has been no recognition or appreciation that a nontoxic NMDA receptor antagonist would have any beneficial application to the treatment of chronic pain or any of its varieties. Surprisingly, it has now been found that a non-toxic NMDA receptor antagonist such as dextromethorphan exhibits significant ameliorating effects on certain types of chronic pain that result from nerve injury.

SUMMARY OF THE INVENTION

In accordance with the present invention, there is provided a method for the treatment of chronic pain which comprises administering to a mammal exhibiting chronic pain a chronic pain-alleviating amount of at least one nontoxic substance that blocks the N-methyl-D-aspartate receptor.

The term "nontoxic" as used herein shall be understood in a relative sense and is intended to designate any substance that has been approved by the United States Food and Drug Administration ("FDA") for administration to humans or, in keeping with established criteria, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 whose toxicities effectively preclude their therapeutic use.

DESCRIPTION OF THE PREFERRED EMBODIMENTS

Figure 1:
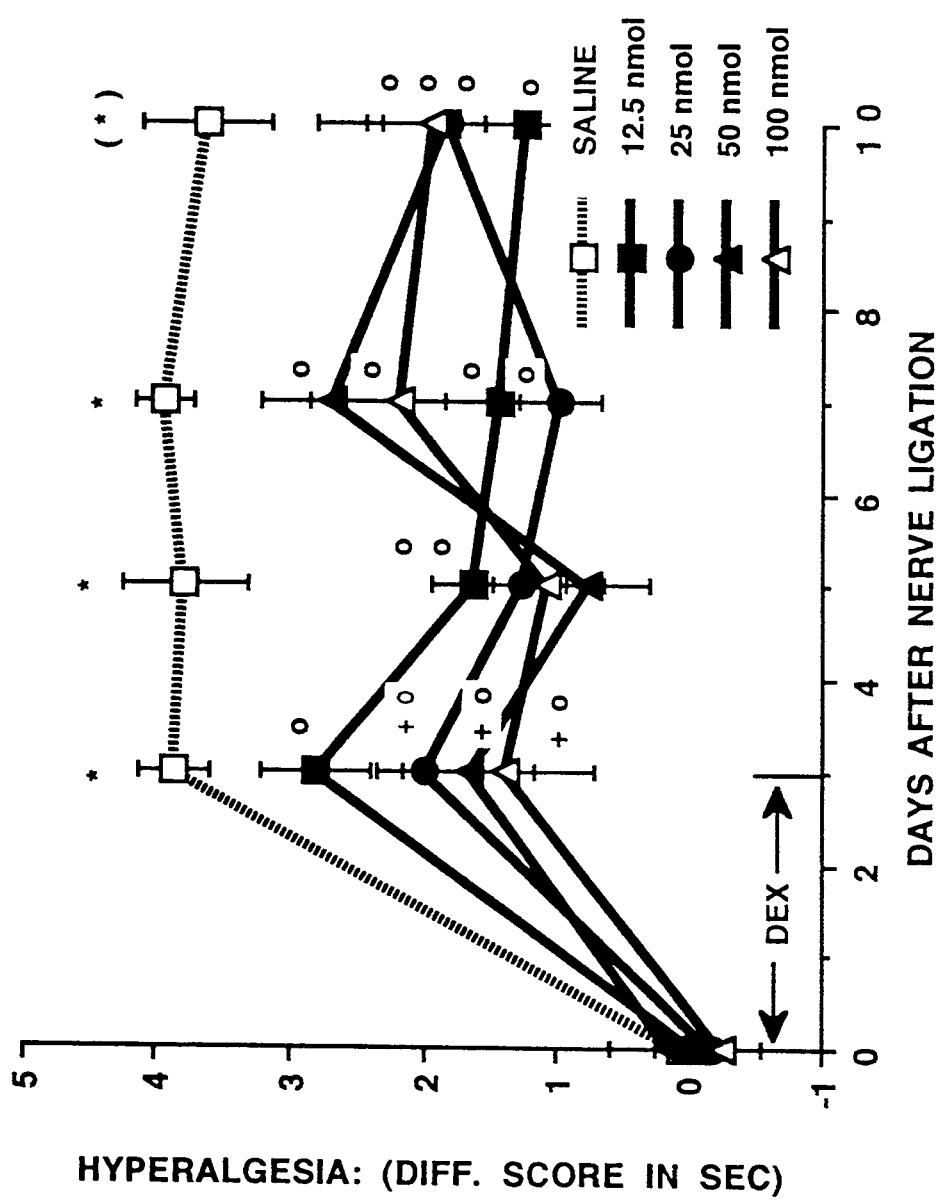
FIG. 1 is a graphical presentation of test results showing the therapeutic effects of intrathecal administration of dextrorphan on hyperalgesia in CCI (chronic constrictive injury) rats.

Among the nontoxic substances that block the NMDA receptor and as such are useful in the practice of the present invention are morphinans such as dextromethorphan ((+)-3-hydroxy-N-methylmorphinan) and dextrorphan ((+)-3-hydroxy-N-methylmorphinan), their mixtures and the pharmaceutically acceptable salts thereof. Other useful nontoxic substances that block the NMDA receptor include ketamine (2-(2-chlorophenyl)-2-(methylamino)cyclohexanone), pyrroloquinoline quinone and cis-4-(phosphonomethyl)-2-piperidinecarboxylic acid.

Administration of the nontoxic NMDA receptor antagonist can be by way of oral administration or by intravenous, intramuscular, subcutanous, intrathecal, epidural or intracerebroventricular injection. Effective dosage levels can vary widely, e.g., from about 0.25 to about 250 mg/day, but actual amounts will, of course, depend on the state and circumstances of the patient being treated. As those skilled in the art recognize, many factors that modify the action of the active substance herein will be taken into account by the treating physician such as the age, body weight, sex, diet and condition of the patient, the time of administration, the rate and route of administration, and so forth. Optimal dosages for a given set of conditions can be ascertained by those skilled in the art using conventional dosage determination tests in view of the experimental data provided herein.

The nontoxic NMDA receptor antagonist will ordinarily be formulated with one or more pharmaceutically acceptable ingredients in accordance with known and established practice. Thus, the NMDA receptor antagonist can be formulated as a liquid, powder, elixir, injectable solution, etc. Formulations for oral use can be provided as hard gelatin capsules wherein the NMDA receptor antagonist is mixed with an inert solid diluent such as calcium carbonate, calcium phosphate or kaolin, or as soft gelatin capsules wherein the NMDA receptor antagonist is mixed with an oleaginous medium, e.g., liquid paraffin or olive oil.

Aqueous suspensions can contain the NMDA receptor antagonist in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g., heptadecaethylene-oxycetanol, or condensation products of ethylene exide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. Such aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide the nontoxic NMDA receptor antagonist in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

The nontoxic NMDA receptor antagonist is advantageously provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

It is also within the scope of this invention to treat chronic pain by administration of the nontoxic NMDA receptor antagonist to the patient prior to, with or following the administration of indicated dosage levels of a local anesthetic such as bupivicaine hydrochloride, chloroprocaine hydrochloride, dibucaine, dibucaine hydrochloride, etidocaine hydrochloride, lidocaine, lidocaine hydrochloride, mepivacaine hydrochloride, piperocaine hydrochloride, prilocaine hydrochloride, procaine hydrochloride, propoxycaine hydrochloride tetracaine, tetracaine hydrochloride, and the like. These local anesthetics will generally be applied directly or close to the nerve that is injured.

The examples that follow are illustrative of the invention.

EXAMPLES 1-3

These examples demonstrate the effectiveness of dextrorphan (Example 1) and ketamine (Example 2) in preventing the development of nociceptive behaviors (hyperalgesia and spontaneous pain-related behaviors) in rats with peripheral mononeuropathy induced by loose ligation of the common sciatic nerve, i.e., chronic constrictive injury (CCI), employing procedures for sciatic nerve ligation described in Bennett et al., *Pain*, 33 (1988) 87–107and in Mao et al., *Brain Res.*, 576 (1992) 254–262.

Adult male Sprague-Dawley rats (Hilltop) weighing 400-500g at the time of surgery were used in these examples. Animals were individually housed in stainless steel cages under a 12 h light cycle (lights on from 0,700 to 19.00 h). Food and laboratory chow were available ad libitum. Animals were implanted with intrathecal (IT) catheters and their right common sciatic nerve was ligated under sodium pentobarbital (50 mg/kg, intraperitoneally) anesthesia. For IT catheter implantation, a segment of polyethylene tubing (PE 10) flushed with 0.4% gentamicin solution was inserted through a small incision at the atlanto-occipital membrane and gently advanced 8.5 cm caudally to the lumbosacral enlargement. The catheter was secured to a skull screw with dental acrylic cement and the rostral end was sealed with putty. For nerve ligation, the right common sciatic nerve was exposed at a level proximal to the sciatic trifurcation and separated from the connective tissue. The nerve was then loosely tied with four chromic gut (4-0) ligatures. The skin incision was closed with a 4-0 silk suture. All CCI rats were injected post-operatively with potassium penicillin (30,000 IU/rat) intramuscularly to prevent infection.

Hyperalgesia to radiant heat was assessed in the CCI rats employing the procedure described in Mao et al., *Brain Res.*, 584 (1992) 28–35 and 576 (1992) 254–262.

Pain threshold was determined by measuring the foot-withdrawal latency defined as the time from the onset of radiant heat to foot withdrawal. The baseline latency was adjusted to 10-11s and the cut-off time was preset to 15s in order to prevent tissue damage. Three test trials were made for each of the rat's hind paws. The mean withdrawal latency (MWL) of three test trials was used to calculate foot-withdrawal latency difference scores (MWL of non-ligated hind paw minus MWL of ligated hind paw). Spontaneous nociceptive behaviors were quantified for each CCI rat by using a spontaneous pain behavior rating method as described in Mao et al., Brain Res., 584 (1992) 28–35 and 576 (1992) 254–262. Each rat was allowed to freely move within an open top transparent plastic cylinder (diameter 19 cm X height 30 cm) and, following an adaptation period of 5 min, the combined duration of two behaviors was recorded over three consecutive 5-min observation periods: (1) the placement of only the medial edge or the heel of the ligated hind paw on the ground, and (b) the lifting of that hind paw. For statistical evaluation, the average score of each animal over the three observation periods was used.

Dextrorphan (12.5, 25, 50 or 100 nmol in 10 μl), ketamine at equivolume and equimolar doses, or equivolume saline vehicle were administered IT at 24-h intervals for the first 4 consecutive days starting 1 h after surgery and ending 30 min prior to testing on day 3 post-surgery (n=6/group). Thermal hyperalgesia was assessed 1 day before surgery (baseline) and then on days 3, 5, 7 and 10 post-surgery. Intrathecal injection was given slowly over a 10-to 15-s period using a Hamilton 50μl syringe and followed by 10 μl (void volume of catheters) of saline to flush the drug into the subarachnoid space.

Figure 2:
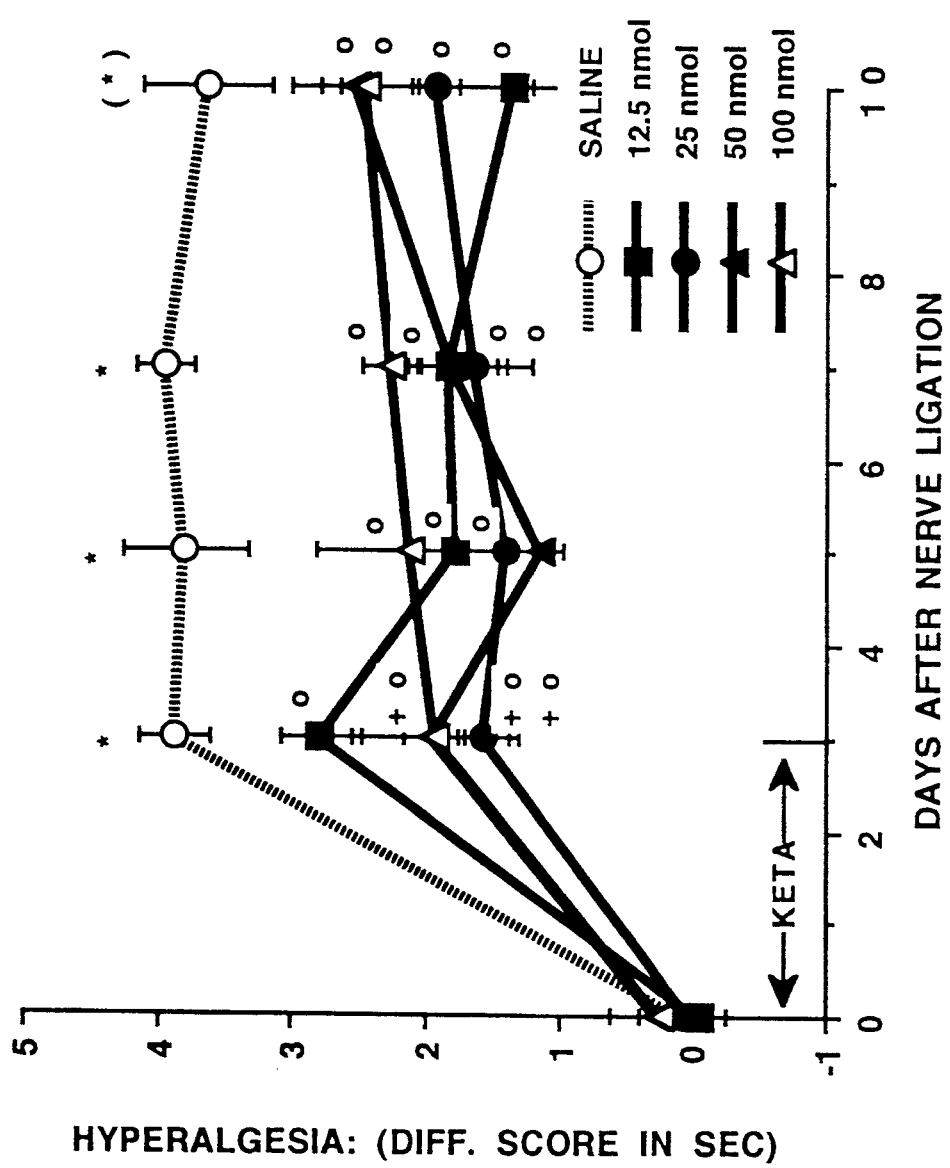
FIG. 2 is a graphical presentation of test results showing the therapeutic effects of intrathecal administration of ketamine on hyperalgesia in CCI rats.

The foot withdrawal latency difference scores for CCI rats treated with dextrorphan over the 10 day post-surgery evaluation period are set forth in FIG. 1 and the scores for the CCI rats treated with intrathecal ketamine are set forth in FIG. 2. The latency difference score shown on the y-axis was obtained by subtracting ipsilateral foot-withdrawal latencies from contralateral foot-withdrawal latencies, and standard errors are presented as vertical lines.

As indicated by these scores, foot withdrawal latency difference scores on day 3 after nerve ligation were reliably higher (3-4s) in CCI rats receiving saline treatment compared to their baseline scores and remained higher for the entire 10 day post-surgery period. Multiple intrathecal treatments with either dextrorphan (FIG. 1) or ketamine (FIG. 2) reliably reduced foot-withdrawal latency difference scores as compared to those of saline-treated CCI rats on days 3, 5 and 7 but, apart from the 12.5-nmol dose groups, not on day 10 post-surgery. This reduction of thermal hyperalgesia continued even after the withdrawal of dextrorphan prior to day 4 following nerve ligation. The foot withdrawal latency difference between two hind paws of CCI rats was due to a reduction of foot-withdrawal latency in the ligated hind paw, since the withdrawal latency of the non-ligated hind paw was unchanged as compared to baseline latencies, indicating the presence of thermal hyperalgesia in CCI rats. The lack of reliable reduction of thermal hyperalgesia in the remaining drug treatment groups on day 10 post-surgery may be due to the small sample size (n=6) of each group. The reduction of thermal hyperalgesia was partially dose related for both compounds on day 3 post-surgery (dextrorphan and ketamine; 100=50=25 nmol >12.5 nmol) but not on the remaining test days (FIGS. 1 and 2

Figure 3:
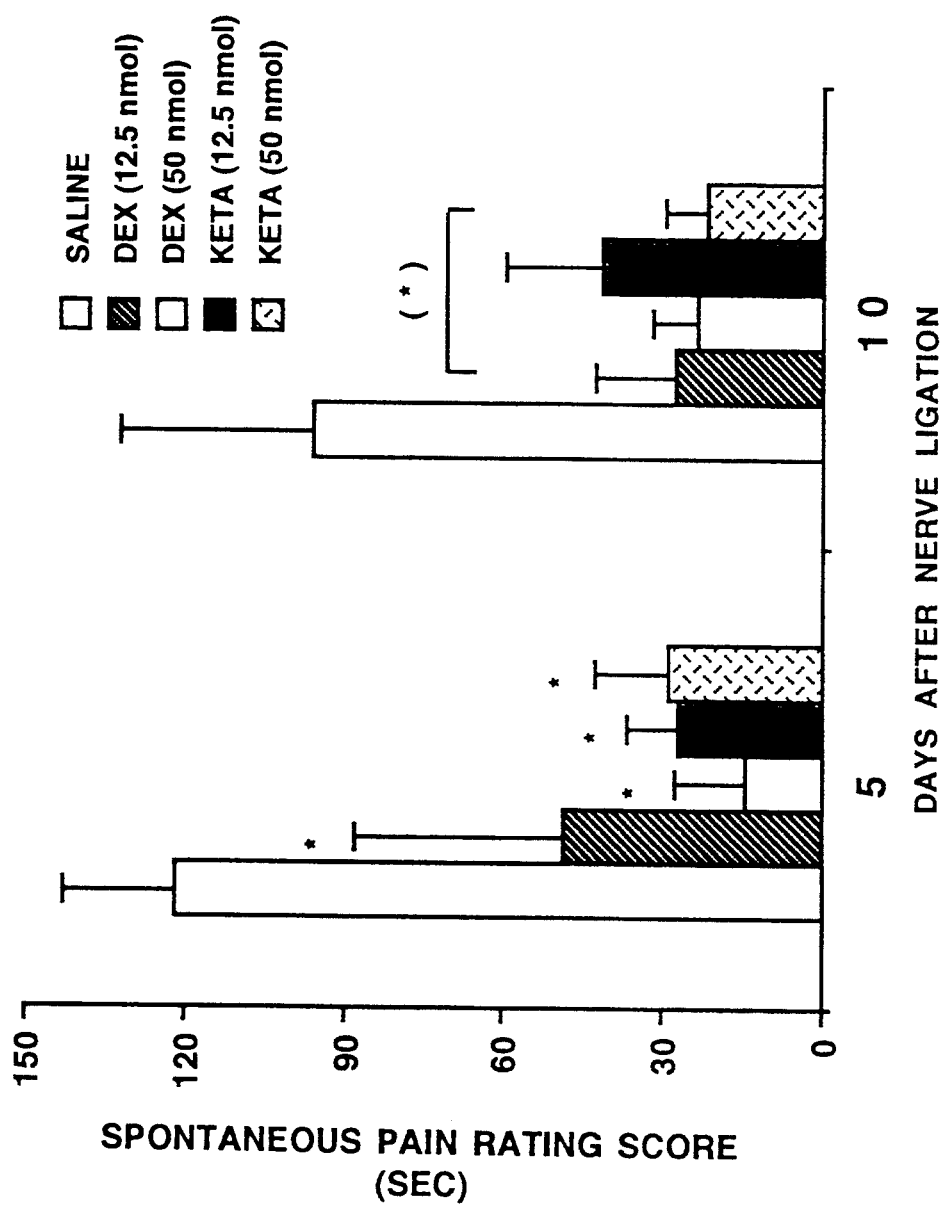
FIG. 3 is a graphical presentation of test results demonstrating attenuation of spontaneous pain-related behaviors in CCI rats treated with dextrorphan or ketamine; and, FIG. 4 is a graphical presentation of test results showing the therapeutic effects of dextrorphan or ketamine, given 3 days after nerve injury, on nociceptive behaviors in CCI rats.

Consistent with their effects on thermal hyperalgesia, multiple treatments with dextrorphan or ketamine (12.5, 50 nmol for each compound) also reduced spontaneous pain-rating scores in CCI rats on day 5 following nerve ligation (FIG. 3) indicating the attenuation of spontaneous pain-related behaviors. Spontaneous pain-rating scores on day 10 post-surgery were, however, not significantly different between the saline group and each of drug treatment groups. This was likely due to the small sample size (n=7/group) since spontaneous pain-rating scores were reliably higher in the saline group as compared to the treatment group pooled from four drug treatment groups.

EXAMPLE 4

This example demonstrates the therapeutic effectiveness of dextrorphan and ketamine on nociceptive behaviors in CCI rats. Unlike examples 1-3 which illustrate prevention, these effects represent the reversal of pain-related behaviors caused by constrictive injury of the sciatic nerve.

Figure 4:
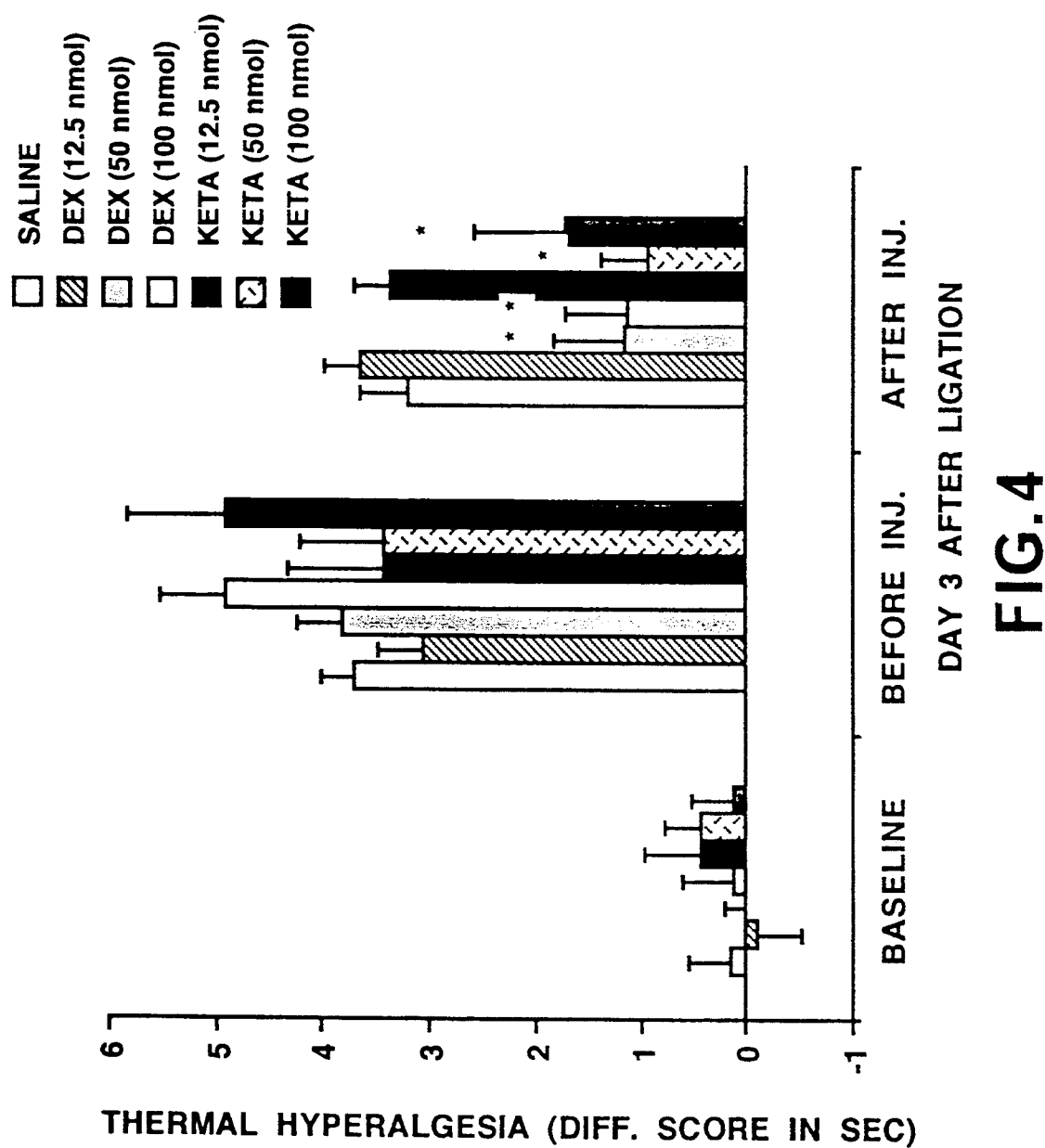

Seven groups (n=7/group) of CCI rats received a single IT treatment with either dextrorphan or ketamine (12.5, 50, and 100 nmol for each compound) or IT saline injection on day 3 after nerve ligation. As shown in FIG. 4, the CCI rats in all 7 groups exhibited thermal hyperalgesia before treatment on day 3 post-surgery as demonstrated by reliably higher foot-withdrawal latency difference scores as compared to baseline latency difference scores. Thirty minutes after each treatment, foot-withdrawal latency difference scores were reliably lower in CCI rats treated with 50 or 100 nmol (but not 12.5 nmol) dextrorphan or ketamine as compared to those receiving a single saline treatment. The reduction of thermal hyperalgesia was nearly complete since latency difference scores in CCI rats treated with dextrorphan or ketamine (50 or 100 nmol) were not significantly different from their baseline scores indicating a potent reduction of thermal hyperalgesia in these CCI rats by an acute, single treatment with dextrorphan or ketamine.

What is claimed is:

1. A method of treating chronic pain which comprises administering to a mammal exhibiting chronic pain a chronic pain-alleviating amount of at least one nontoxic N-methyl-D-aspartate receptor antagonist.

2. The method of claim 1 wherein the nontoxic N-methyl-D-aspartate receptor antagonist is dextromethorphan, dextrorphan, ketamine or pharmaceutically acceptable salt thereof.

3. The method of claim 1 wherein the nontoxic N-methyl-D-aspartate receptor antagonist is provided in sustained release dosage form.

4. The method of claim 1 wherein the nontoxic N-methyl-D-aspartate receptor antagonist is administered prior to, with or following administration to the mammal of a local anesthetic.

5. The method of claim 1 wherein the nontoxic N-methyl-D-aspartate receptor antagonist is administered by intravenous, intramuscular, subcutanous, intrathecal, epidural or intracerebroventricular injection.

6. A method of treating chronic pain in a mammal which comprises administering to a mammal exhibiting chronic pain a chronic pain-alleviating amount of at least one chronic pain alleviating agent selected from the group consisting of dextromethorphan, dextrorphan, ketamine or pharmaceutically acceptable salt thereof.

7. The method of claim 6 wherein the chronic pain alleviating agent is provided in sustained release dosage form.

8. The method of claim 6 wherein the chronic pain alleviating agent is administered prior to, with or following administration to the mammal of a local anesthetic.

9. The method of claim 6 wherein the chronic pain alleviating agent is administered by intravenous, intramuscular, subcutanous, intrathecal, epidural or intracerebroventricular injection.

* * * * *